US007153877B2

(12) United States Patent
Bagchi et al.

(10) Patent No.: US 7,153,877 B2
(45) Date of Patent: Dec. 26, 2006

(54) METHOD AND COMPOSITION FOR PREVENTING OR REDUCING THE SYMPTOMS OF INSULIN RESISTANCE SYNDROME

(75) Inventors: Debasis Bagchi, Concord, CA (US); Harry G. Preuss, Fairfax Station, VA (US); Shil C. Kothari, Concord, CA (US)

(73) Assignee: Interhealth Nutraceuticals Incorporated, Benicia, CA (US)

( * ) Notice: Subject to any disclaimer, the term of this patent is extended or adjusted under 35 U.S.C. 154(b) by 175 days.

(21) Appl. No.: 11/009,266

(22) Filed: Dec. 9, 2004

(65) Prior Publication Data
US 2005/0100614 A1 May 12, 2005

Related U.S. Application Data

(62) Division of application No. 10/265,093, filed on Oct. 4, 2002.

(51) Int. Cl.
*A61K 31/095* (2006.01)
*A61K 31/28* (2006.01)
*A61K 31/35* (2006.01)
*A61K 31/315* (2006.01)
*A61K 31/191* (2006.01)
*A61K 31/194* (2006.01)
*A61K 31/455* (2006.01)
*A61K 31/555* (2006.01)
*A61K 31/7048* (2006.01)
*A61K 33/04* (2006.01)
*A61K 33/24* (2006.01)
*A61K 33/30* (2006.01)
*A61P 3/06* (2006.01)
*A61P 3/08* (2006.01)
*A61P 3/10* (2006.01)
*A61P 5/50* (2006.01)

(52) U.S. Cl. .......................... 514/356; 514/23; 514/24; 514/25; 514/26; 514/27; 514/28; 514/32; 514/33; 514/35; 514/42; 514/45; 514/46; 514/47; 514/48; 514/49; 514/50; 514/51; 514/52; 514/53; 514/54; 514/62; 514/188; 514/456; 514/494; 514/505; 514/506; 514/517; 514/574; 514/706; 514/708; 514/733; 514/824; 514/866; 514/909; 424/641; 424/643; 424/655; 424/656; 424/702; 424/725; 424/750; 424/757; 424/774; 424/776

(58) Field of Classification Search ............... 424/641, 424/643, 655, 656, 702, 725, 750, 757, 774, 424/776; 514/23, 24, 25, 26, 27, 28, 32, 514/33, 35, 42, 45, 46, 47, 48, 49, 50, 51, 514/52, 53, 54, 62, 188, 356, 456, 494, 505, 514/506, 517, 574, 706, 708, 733, 824, 866, 514/909

See application file for complete search history.

(56) References Cited

U.S. PATENT DOCUMENTS

| | | | |
|---|---|---|---|
| 3,764,692 | A | 10/1973 | Lowenstein |
| 4,923,855 | A | 5/1990 | Jensen |
| 4,954,492 | A | 9/1990 | Jensen |
| 5,116,820 | A | 5/1992 | Hiji |
| 5,194,615 | A | 3/1993 | Jensen |
| 5,266,560 | A | 11/1993 | Furman et al. |
| 5,480,657 | A | 1/1996 | Allen |
| 5,536,516 | A | 7/1996 | Moffett et al. |
| 5,543,405 | A | 8/1996 | Keown et al. |
| 5,567,424 | A | 10/1996 | Hastings |
| 5,612,039 | A | 3/1997 | Policappelli et al. |
| 5,626,849 | A | 5/1997 | Hastings et al. |
| 5,656,314 | A | 8/1997 | Moffett et al. |
| 5,716,976 | A | 2/1998 | Bernstein |
| 5,783,603 | A | 7/1998 | Majeed et al. |
| 5,905,075 | A | 5/1999 | Harpe et al. |
| 5,911,992 | A | 6/1999 | Braswell et al. |
| 5,981,510 | A | 11/1999 | Fujiwara et al. |
| 6,034,125 | A | 3/2000 | McLeod |
| 6,048,846 | A | 4/2000 | Cochran |
| 6,100,251 | A | 8/2000 | De la Harpe et al. |
| 6,160,172 | A | 12/2000 | Balasubramanyam et al. |
| 6,203,819 | B1 | 3/2001 | Fine |
| 6,207,714 | B1 | 3/2001 | Clouatre et al. |
| 6,217,898 | B1 | 4/2001 | Cavazza |
| 6,258,848 | B1 | 7/2001 | Fantus |
| 6,291,533 | B1 | 9/2001 | Fleischner |
| 6,352,713 | B1 | 3/2002 | Kirschner et al. |
| 6,383,482 | B1 | 5/2002 | Gorsek |

(Continued)

FOREIGN PATENT DOCUMENTS

EP    0 714 663    6/1996

(Continued)

OTHER PUBLICATIONS

U.S. Appl. No. 60/554,653, filed Mar. 19, 2004, Bagchi et al.

(Continued)

*Primary Examiner*—John Pak
(74) *Attorney, Agent, or Firm*—Fliesler Meyer LLP

(57) ABSTRACT

A method for preventing and or reducing the symptoms of insulin resistance and a related syndrome in persons comprises identifying persons having or at risk for having such symptoms, and administering to them an effective amount of a composition comprising niacin-bound chromium that prevents or reduces the symptoms. Compositions incorporating niacin-bound chromium and additional compounds also are disclosed that are particularly effective in synergistically preventing or reducing these symptoms.

10 Claims, No Drawings

U.S. PATENT DOCUMENTS

| | | |
|---|---|---|
| 6,395,296 B1 | 5/2002 | Balasubramanyam et al. |
| 6,399,089 B1 | 6/2002 | Yegorova et al. |
| 6,413,545 B1 | 7/2002 | Alviar et al. |
| 6,420,350 B1 | 7/2002 | Fleischner |
| 6,441,041 B1 | 8/2002 | Clouatre et al. |
| 6,447,807 B1 | 9/2002 | Clouatre et al. |
| 6,476,071 B1 | 11/2002 | Clouatre et al. |
| 6,482,858 B1 | 11/2002 | Clouatre et al. |
| 6,541,026 B1 | 4/2003 | Siskind |
| 6,579,866 B1 | 6/2003 | McCleary |
| 6,589,566 B1 | 7/2003 | Ueda et al. |
| 6,638,542 B1 | 10/2003 | Nieuwenhuizen et al. |
| 6,809,115 B1 | 10/2004 | Katz et al. |
| 6,967,030 B1 | 11/2005 | Wright et al. |
| 2001/0031744 A1 | 10/2001 | Kosbab |
| 2001/0044469 A1 | 11/2001 | Clouatre et al. |
| 2002/0132219 A1 | 9/2002 | McCleary |
| 2003/0119913 A1 | 6/2003 | Ohia et al. |
| 2003/0133992 A1 | 7/2003 | Bagchi et al. |
| 2003/0207942 A1 | 11/2003 | Bhaskaran et al. |
| 2003/0220329 A1 | 11/2003 | Surwit et al. |
| 2004/0014692 A1 | 1/2004 | Bagchi et al. |
| 2004/0157929 A1 | 8/2004 | Ohia et al. |
| 2004/0186181 A1 | 9/2004 | Bagchi et al. |

FOREIGN PATENT DOCUMENTS

| | | |
|---|---|---|
| JP | 10262610 | 10/1998 |
| WO | WO 89/10357 | 11/1989 |
| WO | WO 98/28989 | 7/1998 |
| WO | WO 99/03464 | 1/1999 |
| WO | WO 00/12080 | 3/2000 |
| WO | WO 00/48983 | 8/2000 |
| WO | WO 00/57729 | 10/2000 |
| WO | WO 02/0788616 | 10/2002 |

OTHER PUBLICATIONS

U.S. Appl. No. 60/628,381, filed Nov. 16, 2004, Bagchi et al.
Separate systems for serotonin and leptin in appetite control, Jason CG Halford et al. The Finnish Medical Society Duodecim, *Ann Med 2000*; 32: 222-232.
Serotonin induces mapk activation in primary cultures of cortical neurons; L.M. Tolbert et al. *Division of Molecular Psychiatry, Yale University*, New Haven, CT, USA, date unavailable.
Effect of hydroxycitric acid on serotonin release from isolated rat brain cortex, by Sunny E. Ohia et al. Department of Pharmacy Sciences, School of Pharmacy and Allied Health Professions, Creighton University, Omaha, NE 68178, date unavailable.
(-)-Hydroxycitrates—The usefulness of (-)-hydroxycitric acid as an obesity regulator is attracting more attention from the food & pharmaceutical industry. Can it be called an ingredient for functional foods? By James Verghese; The World of Ingredients, date unavailable.
Enhancing central and peripheral insulin activity as a strategy for the treatment of endogenous depression—an adjuvant role for chromium picolinate? By M.F. McCarthy; *Medical Hypotheses* (1994) 43: 247-252.
The Diet and health benefits of HCA—How this all-natural diet aid promotes weight loss and inhibits fat production, By Dallas Clouatre, Ph.D. et al. A Keats Good Health Guide (1994).
AIM Metabolite (1999) AIM International, Inc.
Chromium, http://www.supplementdirect.com/research/chromium.html, pp. 1-13, date unavailable.
Anti-Fat Nutrients, by Dallas Clouatre, (1993) Ph.D. Fax Publishing, San Francisco, CA.
Encyclopedia of Nutritional Supplements, The Essential Guide for Improving your Health Naturally, by Michael T. Murray, N.D. (1996) Prima Publishing, Random House, Inc. New York. pp. 194-198.
Beware of New Weight Loss Products, by Pat Kendall, Ph.D., R.D. Food Science and Human Nutrition Specialist, Colorado State University Cooperative Extension Jul. 7, 1999.
Weight Loss—An alternative Medicine Definitive Guide, by Burton Goldberg; AlternativeMedicine.com Books, Tiburon, California, date unavailable.
Herbs and Weight Loss FAQ's; http://herbsforhealth.about.com/library, pp. 1-3, date unavailable.
Evaluating Natural Weight Loss Supplements, http://altmedicine.about.com/library/weekly; pp. 1-8, date unavailable.
Physiological Reviews—Chromium Occurence and Function in Biological Systems, by Walter Mertz, Division of Biochemistry, Walter Reed Army Institute of Research, Walter Reed Army Medical Center, Washington, D.C. The American Physiological Society, vol. 49, No. 2, Apr. 1969, pp. 163-239.
Influence of (-)-hydroxycitrate on lipigenesis in chickens and rat, by Chee H. Romsos, DR; http:www.ncbi.nlm.nih.gov, date unavailable.
Role of fatty acid synthesis in the control of insulin-stimulated glucose utilization by rat adipocytes, by Susan K. Fried, et al. Journal of Lipid Research, vol. 22, 1981, pp. 753-762.
Implications of steroid saponins and sapogenis in the hypocholesterolemic effect of fenugreek, by Yves Sauvalre et al. LIPIDS, vol. 26, No. 3 (1991).
Antidiabetic effects of S-allyl cysteine sufphoxide isolated from garlic *Allium sativum Linn*; Indian Journal of Experimental Biology, vol. 30, Jun. 1992, pp. 523-526.
More direct evidence for a malonyl-CoA-carnitine palmitoyltransferase I interaction as a key event in pancreatic beta-cell signaling, by S. Chen, et al. Diabetes, vol. 43, Issue 7, pp. 878-883, 1994.
Effects of chromium and guar on sugar-induced hypertension in rats, by H.G. Preuss et al. *Clinical Nephrology*, vol. 44, No. 3 (1995).
New Information on (-)-hydroxycitric acid/HCA, by Dallas Clouatre, Ph.D. Clouatre Consulting Group, Sep. 5, 1995.
Current Zinc Intake and Risk of Diabetes and Coronary Artery Disease and Factors Associated with Insulin Resistance in Rural and Urgan Populations of North India, by: Ram B. Singh, et al. *Journal of the American College of Nutrition*, vol. 17, No. 6, pp. 564-570 (1998).
Toward a wholly nutritional therapy for type 2 diabetes, by M.F. McCarty; *Medical hypothesis*, vol. 54, Issue 3, Mar. 2000, pp. 483-487.
Clinical Study on Ephedra-Free Super Citrimax® ; Interhealth, dated Jan. 29, 2004 Press Release.
Researchers Reveal the Beauty of Super CitriMax® —Again; New HCA Study Confirms Super CitriMax® may be the most Effective, All-Natural Diet Ingredient Yet, pp. 1-8, date unavailable.
The Diet and Health Benefits of HCA (Hydroxycitric Acid) How this all-natural diet aid promotes weight loss and inhibits fat production, by Dallas Clouatre, Ph.D. et al. A Good Health Guide, date unavailable.
Increase of fat oxidation and weight loss in obese mice caused by chronic treatment with human growth hormone or a modified C-terminal fragment, by M.A. Heffernan, et al. *International Journal of Obesity* (2001) vol. 25, pp. 1442-1449.
Leptin increases serotonin turnover by inhibition of brain nitric oxide synthesis, by Gioacchino Calapai et al. *The Journal of Clinical Investigation*, Oct. 1999, vol. 104, No. 7, pp. 975-982.
The synthesis aninal experiments and preliminary clinical trial of chrimium (III)-nicotinicacid-amino acids mixed ligand complexes, by Yang, et al. Database CAPLUS, Sch. Pharm, West China Univ. Med. Sci., (Chengdu, China), AN 1988:542370.
Palmeri, Denise, "Metabolife, Metabolite and Chitoslim: Safe Bets for Losing Weight?," ext.colostate.edu, May 2002 pp. 1-4.
Ohia, Sunny E., et al., "Safety and mechanism of appetite suppression by a novel hydroxycitric acid extract (HCA-SX)," *Molecular and Cellular Biochemistry*, vol. 238, pp. 89-103, 2002.
Roy, Sashwati, et al., "Body Weight and Abdominal Fat Gene Expression Profile in Response to a Novel Hydroxycitric Acid-Based Dietary Supplement," *Gene Expression*, vol. 11, pp. 251-262, Feb. 24, 2004.

Shara, Michael, et al., "Physico-chemical properties of a novel (--)-hydroxycitric acid extract and its effect on body weight, selected organ weights, hepatic lipd peroxidation and DNA fragmentation, hematology and clinical chemistry, and histopathological changes over a period of 90 days," *Molecular and Cellular Biochemistry*, vol. 260, pp. 171-186, Oct. 3, 2003.

METHOD AND COMPOSITION FOR PREVENTING OR REDUCING THE SYMPTOMS OF INSULIN RESISTANCE SYNDROME

CROSS REFERENCE TO RELATED APPLICATIONS

This is a division of U.S. patent application Ser. No. 10/265,093, filed Oct. 4, 2002.

BACKGROUND OF THE INVENTION

The present invention relates generally to a method and composition for preventing or reducing the symptoms of insulin resistance syndrome in a person.

An insulin resistance syndrome that has been identified as "Syndrome X" by previous research is a common metabolic disorder affecting more than 75 million Americans to some degree. Insulin resistance is a condition in which the body becomes resistant to its own insulin. The body of the person affected compensates by releasing more insulin, elevating body insulin levels. This elevated insulin level leads to increased risk of a variety of symptoms, including diabetes, obesity, and heart disease.

Syndrome X appears to be highly prevalent in the obese. Individual elements of Syndrome X (obesity, hypertension, lipid disturbances, and glucose intolerance) are frequently encountered during a typical person's life span, and they tend to be increasing apparent as people age, usually becoming most prevalent after age 35. Theoretical considerations suggest that insulin resistance may be a primary factor that plays a causative role in the induction of both obesity and diabetes. Atherogenic risk factors associated with obesity and Syndrome X contribute independently to the development of atherosclerotic disease, and risk of a cardiovascular event increases sharply with the burden of risk factors associated with obesity.

Animal models of Syndrome X, as observed in rats fed high fat diets, exhibit excess accumulation of muscle triglyceride coincident with development of insulin resistance. This also seems to occur in humans; several studies demonstrate increased muscle triglyceride content in insulin resistant states. There is substantial evidence indicating that excess muscle and liver lipid accumulation causes or exacerbates insulin resistance in Syndrome X and in Type II diabetes. Development of strategies to prevent this, therefore, seem worthwhile.

Avoiding weight gain from adolescence to middle age is known to reduce cardiovascular morbidity and mortality. Despite much debate in the past regarding the influence of obesity on health and the benefits of maintaining normal weight, it is clear that changes in weight correlate to changes in several atherogenic risk factors. Recent perspective studies indicate a continuous graded influence of body mass index (BMI), the ratio of weight expressed in kilograms divide by the height meters squared, on the rate of coronary disease development. Increased risk is evident at BMI levels below average, indicating that moderate obesity can be unhealthy. Central obesity, typically including measurements of waist girth or waist to hip ratio, has been shown to be more metabolically disadvantageous than other forms of obesity and, as a consequence, it is considered a strong predictor of cardiovascular disease.

The mechanism whereby obesity and weight gain promote atherogenic risk factors and, in turn, cardiovascular disease is well established. Excess body fat has been shown to increase resistance to insulin action and reduce uptake of glucose by peripheral tissues. Abdominal obesity, in particular, is associated with insulin resistance, hyperinsulinemia, a relative deficiency of lipoprotein lipase, elevated triglycerides, reduced HDL-cholesterol and small dense LDL-particles. Obesity may promote increased absorption in the renal tubules, expanding blood volume and inducing an autonomic imbalance that results in hypertension. In addition, insulin resistance often eventuates into glucose intolerance and diabetes which in turn accelerates atherogenesis.

Obesity is clearly the most prevalent metabolic disorder in the United States, and weight control deserves a high priority to curb cardiovascular disease and the associated predisposing conditions, such as lipidemia, hypertension and glucose intolerance. The benefits of weight control on the major atherogenic risk factors and the insulin resistance syndrome should provide a strong incentive and rationale for control of obesity. There is no other risk factor that affects the cardiovascular risk profile as strongly. It is well known that non-insulin dependent type II diabetes is highly associated with obesity. It has been reported that healthy persons with elevated insulin levels have increased levels of LDL cholesterol, decreased HDL cholesterol and high blood pressure compared with healthy individuals who have normal insulin levels. Diabetes is associated with high blood lipids, hypertension and a tendency of blood platelets to clot, which can block arteries resulting in heart attack or stroke. Diabetes causes a defect in glucose homeostasis. Weight control is a logical first approach to avoid moderate degrees of hypertension, dyslipidemia, glucose tolerance and hyperinsulinemia that constitute Syndrome X.

To overcome glucose tolerance, patients with syndrome X secrete large amounts of insulin. Treatment of Syndrome X should therefore be aimed at: 1) increasing insulin sensitivity; 2) attenuating day-long hyperinsulinemia; and 3) pharmacologic treatment of the specific manifestations of syndrome X, if lifestyle interventions such as weight loss are not entirely successful. The two major lifestyle modulators of insulin action are body weight and physical fitness; the heavier and the more sedentary a patient is, the greater the degree of insulin resistance and compensatory hyperinsulinemia.

However, even with control of weight, many people can still develop Syndrome X. Also, many people find controlling their weight to be difficult, and they are unsuccessful in their attempts. Therefore, pharmacological treatments are needed to help reduce the effects of Syndrome X in persons.

Chromium helps insulin metabolize fat, turn protein into muscle and convert sugar into energy. It is an essential trace element required for normal protein, fat and carbohydrate metabolism. Chromium levels are known to decrease with age, and marginal chromium deficiencies appear to be widespread. Chromium is important for energy production and plays a role in regulating appetite, reducing sugar cravings, and increasing lean body mass.

Niacin-bound chromium (also called chromium nicotinate or chromium polynicotinate) dramatically increases the effectiveness of chromium in a person ingesting it. Normally, chromium is poorly absorbed and utilized by the body. However, researchers have found that the most potent form of chromium in nature is that form bound to the B-vitamin, niacin. Furthermore, previous research discoveries led to the identification of Glucose Tolerance Factor or "GTF", a biologically active form of chromium that facilitates normal insulin function, which is responsible for normal glucose (blood sugar) metabolism. Researchers have found that a particular oxygen-coordinated chromium niacin complex is the most potent form of all, being over eighteen times more potent than the next closest form of niacin-bound chromium.

In 1997, researchers at the University of Texas, Austin, showed that a combination of administration of niacin-bound chromium along with exercise in obese women resulted in a significant weight loss in the women and also lowered the increase in insulin levels when the women were orally fed glucose. In contrast, those taking chromium picolinate, a different form of chromium, were found to show significant weight gain. In 1999, researchers at Georgetown University Medical Center showed that compared to a placebo, niacin-bound chromium caused significant loss of body fat and sparing of muscle (lean body mass) in overweight African-American women. Also, tests on the blood chemistries of the women revealed no significant adverse effects from the ingestion of 600 µg of elemental chromium daily for 2 months. This observation demonstrated the safety of administration of niacin-bound chromium at the tested levels.

In 1994, researchers at Auburn University showed that supplementation with 200 mcgs of niacin-bound chromium significantly lowered moderate levels of cholesterol by an average of 14 percent and improved the ratio of total cholesterol to HDL ("good") cholesterol by 7 percent in male athletes. In 1995, researchers at Georgetown University Medical Center showed that a combination of niacin-bound chromium and soluble fiber (i.e., guar) significantly inhibited sugar-induced high blood pressure in rats. In 1997, researchers at Georgetown University Medical Center showed that niacin-bound chromium inhibited sugar-induced high blood pressure, improved long-term blood sugar status and reduced liver and kidney lipid peroxidation in rats. In 2000, researchers at Georgetown University Medical Center showed that a combination of niacin-bound chromium and grape seed proanthocyanidin extract significantly lowered both total cholesterol levels and LDL ("bad") cholesterol levels by 10 and 14 percent, respectively, in people with elevated blood cholesterol levels.

Diabetic patients have been found to have lower serum chromium levels and a higher chromium excretion rate. Treatment with niacin-bound chromium has been found to improve glucose tolerance in diabetic patients. Dietary trivalent chromium has been shown to have significant beneficial effects on the insulin system.

It has been demonstrated that essential hypertension may be due to insulin perturbations. As high dose chromium supplementation seems nontoxic, chromium may prove to be a useful means to lower blood pressure in some essential hypertensives as well as diabetic hypertensives. It also has been shown that chromium supplementation may prove to be the most useful means to prevent or treat type II diabetes mellitus and related cardiovascular disorders. Chromium supplementation amplifies insulin receptor tyrosine kinase activity, which explains the relationship between chromium and its effects in diabetes. Chromium further reduces vascular smooth muscle calcium loads and thus reduces peripheral vascular resistance in insulin-resistant states.

Recently, the U.S. Department of Agriculture (USDA) found that many middle-age diabetics could overcome their symptoms by taking a chromium supplement. The USDA's findings suggest that very low chromium intakes may be putting millions of Americans on the road to diabetes (and high blood cholesterol) and that the process could be reversed by supplementing with chromium. A separate study found that marginal chromium loss in male athletes resulting in impaired insulin function can be improved by supplementation with niacin-bound chromium.

However, though the above studies demonstrate that administering niacin-bound chromium may serve as a beneficial therapeutic method for reducing or preventing the various symptoms associated with Syndrome X, this has not been entirely effective. Improved methods and compositions, therefore, are necessary to provide for preventing or and reducing the symptoms of Syndrome X in persons. The present invention fulfills this need and provides for further advantages.

SUMMARY OF THE INVENTION

The present invention resides in a method for preventing or reducing the symptoms of insulin resistance in a person, the method comprising: identifying a person suffering from or at risk for suffering from the symptoms; and administering a composition comprising an effective amount of chromium that is bound to niacin that, when administered to the person, prevents or reduces the symptoms of insulin resistance. The method preferably incorporates administering a composition comprising between about 50 and about 1,000 µg chromium, which is bound to niacin, preferably in two doses per day.

In a preferred aspect of the method, the composition incorporates three compounds selected from the following group: (−) hydroxycitric acid, zinc, trans-resveratrol, gymnemic acid, selenium, anthocyanidine, allicin, or saponins.

Preferably, if present, the amount of (−)hydroxycitric acid in the composition is between about 250 and about 2,500 mg, the amount of zinc in the composition is between about 5 and about 50 mg, the amount of trans-resveratrol in the composition is between about 5 and about 50 mg, the amount of gymnemic acid in the composition is between about 50 and about 200 mg, the amount of selenium in the composition is between about 0.025 mg and about 0.1 mg, the amount of anthocyanidins in the composition is between about 5 and about 50 mg, the amount of allicin in the composition is between about 2 and about 8 mg, and the amount of saponins in the composition is between about 100 and about 300 mg.

The present invention also resides in a composition comprising chromium bound to niacin and three compounds selected from the group consisting of (−) hydroxycitric acid, zinc, trans-resveratrol,. gymnemic acid, selenium, anthocyanidins, allicin, and saponins. Preferred compositions include amounts of these compounds in the above-referenced amounts.

DETAILED DESCRIPTION OF THE PREFERRED EMBODIMENTS

The present invention resides in a method for preventing or reducing the symptoms of Syndrome X in a person, incorporating a step of identifying a person having the Syndrome, and then administering an amount of chromium bound to niacin to the person sufficient to prevent or reduce the symptoms of the Syndrome. The present invention also resides in compositions incorporating chromium bound to niacin that, when ingested in sufficient quantity by a person, prevent or reduce the symptoms of Syndrome X in the person.

The method of the present invention involves first identifying a person having Syndrome X. A diagnosis of Syndrome X is made based on observing some or all of the following common symptoms: impaired glucose tolerance, hyperinsulinemia, diabetes, hypertriglyceridemia, elevated LD cholesterol, low HDL cholesterol, hypertension, diabetes, and hypertension. Then, the person is administered an effective amount of chromium bound to niacin, on a daily basis. Preferably, the amount of chromium, which is bound to niacin, administered to an adult ranges from about 100 to about 1000 micrograms per day, taken in two daily doses. The niacin-bound chromium preferably is administered orally in a variety of forms, including capsule, tablet, beverage, food additive, powder, liquid, or food.

Preferred aspects of the method of the present invention involve administration of additional compounds along with the chromium bound to niacin, including: one or more of the following: (−)hydroxycitric acid; zinc, preferably from zinc methionine; trans-resveratrol; gymnemic acid; selenium; anthocyanidins, preferably from bilberry, blueberry, or grape seed extracts; allicin, preferably from garlic; and saponins, preferably from fenugreek. These components work synergistically with the chromium bound to niacin to improve its function in preventing or reducing the symptoms of Syndrome X. Particularly preferred compositions administered include any three of the components in the following amounts: 50 to 1000 μg niacin-bound chromium; 250 to 2500 mg (−)hydroxycitric acid; 5 to 50 mg zinc; 1 to 5 mg trans-resveratrol; 50 to 200 mg gymnemic acid; 0.025 to 0.1 mg selenium; 5 to 50 mg anthocyanidins; 2 to 8 mg allicin; and 100 to 300 mg saponins.

EXAMPLE

Studies were conducted to evaluate the efficacy of a combination of natural products, including chromium bound to niacin, on lowering high blood pressure, one of the particular symptoms commonly associated with Syndrome X. One half of a group of 100 normotensive rats were fed a diet containing the following: chromium nicotinate at a human equivalency dosage of 400 μg of elemental chromium (marketed under the brand name ChromeMate by InterHealth Nutraceuticals of Benicia, Calif.), zinc methionine (marketed under the brand name OptiZinc by InterHealth Nutraceuticals), and grape seed extract incorporating proanthocyanidins (marketed under the brand name ActiVin by InterHealth Nutraceuticals). The rats that were placed on diets containing supplemental chromium nicotinate had significantly lowered blood pressure and lipid peroxidation in their livers and kidneys than rats fed normal diets. Sugar-induced hypertension also was reduced in the rats, along with hepatic and renal lipid peroxidation and glycosylated hemoglobin levels.

Although the invention has been diclosed in detail with reference only to the prefered embodiments, those skilled in the art will appreciate that additional methods and compositions can be made without departing from the scope of the invention.

We claim:

1. A composition comprising chromium bound to niacin and three compounds selected from the group consisting of (−) hydroxycitric acid, zinc, trans-resveratrol, gymnernic acid, selenium, an anthocyanidin, allicin, and fenugreek.

2. A composition as defined in claim 1, wherein the composition further comprises between about 50 and about 1,000 μg chromium bound to niacin.

3. A composition as defined in claim 1, wherein the composition further comprises between about 250 and about 3,000 mg (−)hydroxycitric acid.

4. A composition as defined in claim 1, wherein the composition further comprises between about 5 and about 50 mg zinc.

5. A composition as defined in claim 1, wherein the composition further comprises between about 5 and about 100 mg trans-resveratrol.

6. A composition as defined in claim 1, wherein the composition further comprises between about 50 and about 200 mg gymnemic acid.

7. A composition as defined in claim 1, wherein the composition further comprises between about 0.025 and about 0.1 mg selenium.

8. A composition as defined in claim 1, wherein the composition further comprises between about 5 and about 100 mg of an anthocyanidin.

9. A composition as defined in claim 1, wherein the composition further comprises between about 2 and about 8 mg allicin.

10. A composition as defined in claim 1, wherein the composition further comprises between about 100 and about 300 mg of fenugreek.

* * * * *